United States Patent
Zhang et al.

(10) Patent No.: US 11,702,705 B2
(45) Date of Patent: Jul. 18, 2023

(54) METHOD FOR DETECTING PARASITIC INFECTION AND KIT

(71) Applicant: XIANGYA HOSPITAL CENTRAL SOUTH UNIVERSITY, Hunan (CN)

(72) Inventors: Zhuohua Zhang, Hunan (CN); Zhengqing Wan, Hunan (CN); Jie Ling, Hunan (CN)

(73) Assignee: XIANGYA HOSPITAL CENTRAL SOUTH UNIVERSITY, Hunan (CN)

( * ) Notice: Subject to any disclaimer, the term of this patent is extended or adjusted under 35 U.S.C. 154(b) by 344 days.

(21) Appl. No.: 16/628,259

(22) PCT Filed: Jun. 28, 2018

(86) PCT No.: PCT/CN2018/093254
§ 371 (c)(1),
(2) Date: Jan. 2, 2020

(87) PCT Pub. No.: WO2019/007251
PCT Pub. Date: Jan. 10, 2019

(65) Prior Publication Data
US 2020/0216915 A1    Jul. 9, 2020

(30) Foreign Application Priority Data
Jul. 2, 2017 (CN) .......................... 201710554315.4

(51) Int. Cl.
| | | |
|---|---|---|
| *C12Q 1/68* | (2018.01) | |
| *C12Q 1/6888* | (2018.01) | |
| *C12Q 1/6883* | (2018.01) | |
| *C12Q 1/6893* | (2018.01) | |

(52) U.S. Cl.
CPC ......... *C12Q 1/6888* (2013.01); *C12Q 1/6883* (2013.01); *C12Q 1/6893* (2013.01)

(58) Field of Classification Search
None
See application file for complete search history.

(56) References Cited

FOREIGN PATENT DOCUMENTS

| CN | 103374615 A | 10/2013 | | |
|---|---|---|---|---|
| CN | 104619858 A | 5/2015 | | |
| CN | 105018613 A | 11/2015 | | |
| WO | 2014019275 A1 | 2/2014 | | |
| WO | WO2014/019275 | * | 2/2014 | ............... C12Q 1/68 |
| WO | WO 2014019275 A1 | * | 2/2014 | ............... C12Q 1/68 |

OTHER PUBLICATIONS

Joiner et al. Toxoplasma gondii: a Protozoan for the Nineties (1993) Infection and Immunity 61:4 1169-1172. (Year: 1993).*
Scholar et al. xPharm: The Comprehensive Pharmacology Reference, 2007. (Year: 2007).*
Wichmann et al. Diagnosing Schistosomiasis by Detection of Cell-Free Parasite DNA in Human Plasma (2009) PLoSNTDS 3:4 e422 9 pages. (Year: 2009).*
Imwong et al. High-Throughput Ultrasensitive Molecular Techniques for Quantifying Low-Density Malaria Parasitemias (2014) Journal of Clinical Microbiology 52:9 3303-3309 . (Year: 2014).*
Chaya et al. Polymerase Chain reaction for the diagnosis of cystic echinococcosis from urine, serum and cyst fluid (2014) Tropical Parasitology 4:1 p. 43-45 (Year: 2014).*
International Search Report for PCT/CN2018/093254 dated Oct. 8, 2018, ISA/CN.
Wichmann. D. et al. "Diagnosing Schistosomiasis by Detection of Cell-Free Parasite DNA in Human Plasma" PLoS Neglected Tropical Diseases. vol. 3. No. (4). Apr. 21, 2009 (Apr. 21, 2009), article e422, see "Materials and Methods."
Wang Dong et al. "Diagnosis of Pneumocystis Jirovecii Pneumonia with Serum Cell-free DNA in Non-HIV-infected Immunocompromised Patients" Oncotarget, vol. 8, No. (42), May 20, 2017 (May 20, 2017), pp. 71946-71953, see p. 71947, right-hand col., line 10 to p. 71948, left-hand col., line 2.
The 1st Office Action dated Jan. 21, 2022 for the Chinese Patent Application No. 201880004078.7.

* cited by examiner

*Primary Examiner* — Jehanne S Sitton
(74) *Attorney, Agent, or Firm* — Yue (Robert) Xu; Apex Attorneys at Law, LLP

(57) ABSTRACT

The present invention provides a method for testing the DNA of the source of the parasite in a sample, a method for diagnosing, using the testing method, whether a host object is suffered with a parasitic infection, a method for determining a treatment effect on a parasitic infection, and a method for screening a candidate treatment of a parasitic infection. Also provided is a kit for the methods.

17 Claims, No Drawings
Specification includes a Sequence Listing.

SEQUENCE LISTING

```
<160> NUMBER OF SEQ ID NOS: 32

<210> SEQ ID NO 1
<211> LENGTH: 21
<212> TYPE: DNA
<213> ORGANISM: Artificial
<220> FEATURE:
<223> OTHER INFORMATION: Primer

<400> SEQUENCE: 1
cactgtgacg tcatctggcc t                                        21

<210> SEQ ID NO 2
<211> LENGTH: 23
<212> TYPE: DNA
<213> ORGANISM: Artificial
<220> FEATURE:
<223> OTHER INFORMATION: Primer

<400> SEQUENCE: 2
tcaggtgacg taatggaggg tct                                      23

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
tctgctgctt gcattcacac                                          20

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
caaatgctcg gtacaccacg                                          20
```

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
gtcggtcgca ttagtagctc                                           20

<210> SEQ ID NO 6
<211> LENGTH: 21
<212> TYPE: DNA
<213> ORGANISM: Artificial
<220> FEATURE:
<223> OTHER INFORMATION: Primer

<400> SEQUENCE: 6
aacaaaccga acacaccaaa c                                         21

<210> SEQ ID NO 7
<211> LENGTH: 22
<212> TYPE: DNA
<213> ORGANISM: Artificial
<220> FEATURE:
<223> OTHER INFORMATION: Primer

<400> SEQUENCE: 7
ctgcaatagc acccaattca ca                                        22

<210> SEQ ID NO 8
<211> LENGTH: 22
<212> TYPE: DNA
<213> ORGANISM: Artificial
<220> FEATURE:
<223> OTHER INFORMATION: Primer

<400> SEQUENCE: 8
gaaggagtat cgttggtacg ct                                        22

<210> SEQ ID NO 9
<211> LENGTH: 22
<212> TYPE: DNA
<213> ORGANISM: Artificial
<220> FEATURE:
<223> OTHER INFORMATION: Primer

<400> SEQUENCE: 9
ttcgtgctac gactttctcc ac                                        22

<210> SEQ ID NO 10
<211> LENGTH: 23
<212> TYPE: DNA
<213> ORGANISM: Artificial
<220> FEATURE:
<223> OTHER INFORMATION: Primer

<400> SEQUENCE: 10
ggagtgcaaa tgaagtagat gcg                                       23

<210> SEQ ID NO 11
<211> LENGTH: 19
<212> TYPE: DNA
<213> ORGANISM: Artificial
<220> FEATURE:
<223> OTHER INFORMATION: Primer

<400> SEQUENCE: 11
ccacccagcg aggtacaag                                                    19

<210> SEQ ID NO 12
<211> LENGTH: 22
<212> TYPE: DNA
<213> ORGANISM: Artificial
<220> FEATURE:
<223> OTHER INFORMATION: Primer

<400> SEQUENCE: 12
agtggtttat ccctcggttc tg                                                22

<210> SEQ ID NO 13
<211> LENGTH: 20
<212> TYPE: DNA
<213> ORGANISM: Artificial
<220> FEATURE:
<223> OTHER INFORMATION: Primer

<400> SEQUENCE: 13
tggcgcaaca ccttgtagat                                                   20

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
gaaggtgaag gtgccgaaga                                                   20

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
agtagcggaa cggtggattt                                                   20

<210> SEQ ID NO 16
<211> LENGTH: 20
<212> TYPE: DNA
<213> ORGANISM: Artificial
<220> FEATURE:
<223> OTHER INFORMATION: Primer

<400> SEQUENCE: 16
acaatggccg gtagtgaaga                                                   20

<210> SEQ ID NO 17
<211> LENGTH: 21
<212> TYPE: DNA
<213> ORGANISM: Artificial
<220> FEATURE:
<223> OTHER INFORMATION: Primer

<400> SEQUENCE: 17
gtttcacacc gacaactgca a                                                 21

<210> SEQ ID NO 18

```
<211> LENGTH: 19
<212> TYPE: DNA
<213> ORGANISM: Artificial
<220> FEATURE:
<223> OTHER INFORMATION: Primer

<400> SEQUENCE: 18
tgagtcgaag gcgaacacc                                                    19

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
ggatccgtcg atgttagcgt                                                   20

<210> SEQ ID NO 20
<211> LENGTH: 20
<212> TYPE: DNA
<213> ORGANISM: Artificial
<220> FEATURE:
<223> OTHER INFORMATION: Primer

<400> SEQUENCE: 20 ccgcccataga gggtagatgc                                                  20

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
cgggacacat cctaactggt                                                   20

<210> SEQ ID NO 22
<211> LENGTH: 20
<212> TYPE: DNA
<213> ORGANISM: Artificial
<220> FEATURE:
<223> OTHER INFORMATION: Primer

<400> SEQUENCE: 22
ccggtcatcc atggggattg                                                   20

<210> SEQ ID NO 23
<211> LENGTH: 20
<212> TYPE: DNA
<213> ORGANISM: Artificial
<220> FEATURE:
<223> OTHER INFORMATION: Primer

<400> SEQUENCE: 23
cagaggctcg tttgtggtca                                                   20

<210> SEQ ID NO 24
<211> LENGTH: 24
<212> TYPE: DNA
<213> ORGANISM: Artificial
<220> FEATURE:
<223> OTHER INFORMATION: Primer

<400> SEQUENCE: 24
```
ggtgcacatt aaataccaaa accc                                          24

<210> SEQ ID NO 25
<211> LENGTH: 22
<212> TYPE: DNA
<213> ORGANISM: Artificial
<220> FEATURE:
<223> OTHER INFORMATION: Primer

<400> SEQUENCE: 25
agcactcctc atcagtcaac tc                                            22

<210> SEQ ID NO 26
<211> LENGTH: 24
<212> TYPE: DNA
<213> ORGANISM: Artificial
<220> FEATURE:
<223> OTHER INFORMATION: Primer

<400> SEQUENCE: 26
ctgaaacatg ctaaaggtat gcgt                                          24

<210> SEQ ID NO 27
<211> LENGTH: 89
<212> TYPE: DNA
<213> ORGANISM: Artificial
<220> FEATURE:
<223> OTHER INFORMATION: Internal control fragment

<400> SEQUENCE: 27
cactgtgacg tcatctggcc tgcagcaaag gtatcatcgg catattctaa gtcagttcaa   60
ctacctagac cctccattac gtcacctga                                     89

<210> SEQ ID NO 28
<211> LENGTH: 84
<212> TYPE: DNA
<213> ORGANISM: Artificial
<220> FEATURE:
<223> OTHER INFORMATION: Internal control fragment

<400> SEQUENCE: 28
tctgctgctt gcattcacac gcagctcaaa agtgtcccag gtctactgaa accccgaag    60 acctcgtggt gtaccgagca tttg                                          84

<210> SEQ ID NO 29
<211> LENGTH: 83
<212> TYPE: DNA
<213> ORGANISM: Artificial
<220> FEATURE:
<223> OTHER INFORMATION: Internal control fragment

<400> SEQUENCE: 29
ctgcaatagc acccaattca cagcatcaag ttccaagcac agtcattcgc tctactcgac   60
tagcgtacca acgatactcc ttc                                           83

<210> SEQ ID NO 30
<211> LENGTH: 77
<212> TYPE: DNA
<213> ORGANISM: Artificial
<220> FEATURE:
<223> OTHER INFORMATION: Internal control fragment

<400> SEQUENCE: 30

-continued

```
ttcgtgctac gactttctcc accgtcatgg cagtcacgct ctaatccatc gcttcgcatc        60
tacttcattt gcactcc                                                       77

<210> SEQ ID NO 31
<211> LENGTH: 75
<212> TYPE: DNA
<213> ORGANISM: Artificial
<220> FEATURE:
<223> OTHER INFORMATION: Internal control fragment

<400> SEQUENCE: 31
ccacccagcg aggtacaagc caatgattcg gttagtctgc tgatggctcg cttcagaacc        60
gagggataaa ccact                                                         75

<210> SEQ ID NO 32
<211> LENGTH: 84
<212> TYPE: DNA
<213> ORGANISM: Artificial
<220> FEATURE:
<223> OTHER INFORMATION: Internal control fragment

<400> SEQUENCE: 32
tggcgcaaca ccttgtagat cccgtcatcg tcaatgatca gttgaggtgg ttgggacatc        60
gctttcttcg gcaccttcac cttc                                               84
```

METHOD FOR DETECTING PARASITIC INFECTION AND KIT

CROSS REFERENCE TO RELATED APPLICATIONS

This application is a US National Phase application based upon PCT Application No. PCT/CN2018/093254, which claims the priority of Chinese Patent Application No. CN 201710554315.4, filed on Jul. 2, 2017, and titled with "METHOD FOR DETECTING PARASITIC INFECTION AND KIT", and the disclosures of which are hereby incorporated by reference.

SEQUENCE LISTING

Sequence Listing is being submitted as an ASCII text file via EFS-Web, file name "190129-APXU-XIANGYA-Sequence-Listing.txt", size 6.10 KB, created on 1/2/2020, the content of which is incorporated herein by reference.

FIELD

The present invention relates to the detection of parasitic infection, and specifically to the determination of parasitic infection status by detecting parasite cell-free DNA in a subject's body fluids, such as blood. The invention also relates to a detection kit and use of the kit for detecting parasitic infection.

BACKGROUND

Parasitic diseases are caused by invasion of parasites into a human body. Due to the fact that the insect species and the parasitic sites are different, the pathological changes and the clinical manifestation vary. This type of disease is widespread and can be found all over the world, especially in tropical and subtropical areas. Parasitic infections are often asymptomatic or at least asymptomatic in the early stage of infection. In order to determine whether the human body is infected by parasites at an early stage, effective early detection methods are needed to provide timely interventional treatment.

Echinococcosis is a severe zoonotic parasitic disease. There are two main types of echinococcosis, one is cystic echinococcosis caused by *Echinococcus granulosus* infection and the other is alveolar echinococcosis caused by *Echinococcus multilocularis* infection. In alveolar echinococcosis, the parasite infiltrated into host tissues and the wall of the cysts were thin, which makes it difficult to be removed completely. Therefore, alveolar echinococcosis also regard as parasitic tumor. The main parasitic site of *Echinococcus* is the liver, and it may also be found in the lung and brain. Its pathogenic effects are mainly manifested in mechanical compression, toxin effects, allergic reactions, etc. In the late stage of the disease, huge cysts are formed in the parasitic site, compressing the surrounding normal tissues, thereby causing irreversible damages. In recent years, with the development of tourism, the migration of population and the sharp increase in domestic dogs, echinococcosis has become a worldwide epidemic disease, which seriously affects the world's public health and economic development. In China, echinococcosis is primarily endemic in western provinces such as Tibet, Xinjiang, Qinghai, Sichuan, and Inner Mongolia. With the implementation of the national "Belt and Road" plan, the prevention and treatment of echinococcosis has received increasing attention, and the need for establishing effective screening and diagnosing methods is urgent.

The current diagnosis of echinococcosis is a comprehensive diagnosis manner based on epidemiological history, clinical manifestations, imaging characteristics, tissue biopsy, and laboratory tests (mainly serum immunological tests).

The cysts formed due to infection can be observed intuitively by imaging examination, which can well support the clinical diagnosis, so it is the preferred method for echinococcosis diagnosis at present. However, imaging examination is susceptible to local tissue conditions, sometimes it is difficult to make a definite determination. In addition, it has a high requirement for equipment, making it unsuitable for screening test.

Etiological examination (tissue biopsy) is the "gold standard" for detecting echinococcosis, which can directly visualize the worm body and make a clear diagnosis. However, sampling is difficult for etiological examination, since direct puncture may cause *Echinococcus* to diffuse from the ruptured cysts into the abdominal cavity.

However, both imaging and etiological examinations have to be performed after the formation of prominent cysts, and it is difficult to detect *Echinococcu* infection in early stage, that is, before clinical symptoms appear.

Immunological examinations can detect echinococcosis before clinical manifestations appear, which is earlier than imaging examinations. The commonly used immunological tests include enzyme-linked immunosorbent assay (ELISA), indirect hemagglutination test (IHA), complement fixation test (CFT), and indirect fluorescent antibody test (IFA). These methods have their own advantages and disadvantages in detecting echinococcosis, but the main disadvantages of them are the presence of non-specific reactions and cross-reactivity, producing a certain false positive rate. Also, it is difficult to distinguish between new infections and previous infections, so it is not suitable for real-time monitoring of the disease.

Chinese Patent Application Publication CN103374615A discloses a PCR detection kit for detecting cystic echinococcosis in dogs, in which PCR amplification is used to detect 12S rDNA of *Echinococcus granulosus* contained in the feces of an animal subject to determine whether it has echinococcosis. Similarly, Chinese Patent Application Publications CN105018613A and CN105925724A respectively disclose methods using PCR amplification to detect *Echinococcus* specific DNA in the feces of animal subjects such as foxes to determine whether the animal subject has echinococcosis. The definitive hosts of *Echinococcus* are animals such as dogs, the intestine of which contains adult worms and the feces of which contains large amounts of eggs. Unfortunately, human is intermediate host of *Echinococcus*, with no adult worms in the intestine and no eggs in the feces, so that these methods cannot be applied to humans.

Patients with parasitic diseases (such as echinococcosis) often miss the best opportunity for treatment due to lack of effective screening and diagnostic methods. There is still a need for effective early detection methods for parasitic infections, so as to timely detect parasitic infections, and implement therapeutic interventions as early as possible.

SUMMARY

The inventors have unexpectedly found that cell-free DNA derived from parasites (such as *Echinococcus*) is present in the body fluids (such as blood, saliva and urine) of the host that is infected with parasites (such as *Echinococcus*). By selectively enriching and specifically detecting the parasite-derived cell-free DNA in the host body fluid using the method of the present invention, it can be determined whether the host has been infected with a parasite. The parasite-derived DNA in the host body fluid can be detected by the method of the present invention even before the clinical symptoms are found. Therefore, parasitic infection can be detected in early stage of the infection, which can give a guide for the therapeutic intervention for parasitic infections as well as monitor the effect of treatments for parasitic diseases. Based on the above, the present invention has been completed.

In the first aspect, the present disclosure provides a method of detecting parasite-derived DNA in a sample, comprising:
1) extracting DNA from the sample;
2) selectively enriching the parasite-derived DNA in the DNA obtained in step 1);
3) subjecting the DNA enriched in step 2) to high-throughput sequencing; and
4) analyzing the sequencing result of step 3), wherein the presence of the parasite-derived DNA sequence in the sequencing result indicates that the sample contains the parasite-derived DNA.

In one embodiment, the sample is a body fluid sample, preferably a blood, saliva and/or urine sample, particularly a serum and/or plasma sample. The body fluid sample may be from a mammal, such as a human.

In another embodiment, the parasite is selected from the group consisting of protozoan, nematode, trematode and cestoda, particularly *Ancylostoma, Ascaris, Schistosoma, Echinococcus, Enterobius, Toxoplasma, Amoeba*, and more particularly *Echinococcus*, such as *Echinococcus granulosus* and/or *Echinococcus multilocularis*.

In another embodiment, in the selective enrichment of step 2), an independent DNA that does not participate in the enrichment amplification and does not affect the enrichment amplification is used as a reference to normalize different samples for comparison; the independent DNA is, for example, λ phage genomic DNA, and human genomic DNA in the sample can also be considered as a reference for normalizing.

In a second aspect, the present disclosure provides a method for determining whether a host is suffering from a parasitic infection, comprising:
1) providing a sample from the host;
2) detecting the presence of parasite-derived DNA in the sample using the method according to the first aspect;
3) according to the result of step 2), if the parasite-derived DNA is present in the sample, it is determined that the host is suffering from parasite infection.

In addition, the present disclosure also provides a method for treating a parasitic infection in a host, comprising: performing the method of the second aspect of the present disclosure to diagnose whether the host subject is suffering from a parasitic infection; If the host subject is suffering from a parasitic infection, treating the same for the parasitic infection.

In a third aspect, the present invention provides a method for determining the efficacy of a parasitic infection treatment in a host, comprising:
1) providing a sample from the host received parasite infection treatment;
2) detecting the presence of parasite-derived DNA in the sample using the method according to the first aspect;
3) according to the result of step 2), if there is no parasite-derived DNA or less amount of parasite-derived DNA in the sample compared to the amount before the treatment, the parasitic infection in the host is indicated to have been treated.

In a fourth aspect, the present disclosure provides a method for screening treatment method for a parasitic infection, comprising:
1) treating a host in need thereof with a candidate treatment for parasitic infection;
2) detecting the presence of parasite-derived DNA in the sample from the host using the method according to the first aspect;
3) according to the result of step 2), if there is no parasite-derived DNA or less amount of parasite-derived DNA in the sample compared to the amount before the treatment, the candidate treatment for parasitic infection is indicated effective.

In a fifth aspect, the present disclosure provides a kit for detecting the presence of parasite-derived DNA in a sample, comprising: a reagent for selectively enriching parasite-derived DNA in a sample, and an instruction for use.

In one embodiment, the kit is used in the method according to any one of the first to fourth aspects of the present disclosure. Accordingly, in another aspect, the present invention also provides a kit for use in the method according to any one of the first to fourth aspects of the present disclosure. In one embodiment of these kits, the sample to be detected is a body fluid sample, preferably a blood, saliva and/or urine sample, particularly a serum and/or plasma sample. The body fluid sample may be from a mammal, such as human. In addition, the kit of the present disclosure may further include a drug for treating parasite infection to use the kit to treat a parasite infection in a host.

In a specific embodiment, the kit further comprises at least one reagent selected from the group consisting of a DNA extraction reagent, a selective enrichment reagent (such as a PCR reagent), and a high-throughput sequencing reagent.

Compared with the methods for detecting parasitic diseases (such as echinococcosis) known in the prior art, the technical solution of the present disclosure provides at least one of the following advantages or other aspects: no requirement to extract DNA from parasites; capability of detecting trace amount of parasite-derived cell-free DNA with the only need to extract cell-free DNA from host body fluid samples, thereby reducing the task of collecting samples during detection to collecting only a small amount of peripheral blood or urine fluid samples.

The beneficial effect of the present disclosure are reflected in at least one of the following aspects or other: high level of evidence: direct detection of parasite DNA with diagnostic significance consistent with pathogenic examination; extremely high sensitivity: based on selective enrichment reactions such as PCR, single-molecule resolution is obtained, making it suitable for early detection of infections; very high specificity: it can be designed to have no cross-reaction with other pathogens and can track disease changes in real time; non-invasive: only one tube of peripheral blood needs to be collected without operations that cause substantial trauma, such as tissue biopsy or surgery, greatly improving patient compliance and/or feasibility; simplicity: when used as a screening tool, no large-scale instrument is required at the scene.

DETAILED DESCRIPTION

Unless specifically indicated, terms used herein have their ordinary meanings as understood by a person of ordinary skill in the art. Explanations of some terms used herein are listed below. Unless otherwise specified, the definitions of these terms shall prevail.

The term "selected from" means selecting from a large number of candidate targets, and can be any one or more of them.

In the present disclosure, when describing the length of a double-stranded polynucleotide such as DNA, "base pair" may be used. For example, when it is recited that a double-stranded polynucleotide such as DNA is n base pairs in length, this means that the double-stranded polynucleotide such as DNA has n nucleotides in one strand.

In a first aspect, the present invention provides a method of detecting parasite-derived DNA in a sample, comprising:
1) extracting DNA from the sample;
2) selectively enriching the parasite-derived DNA in the DNA obtained in step 1);
3) subjecting the DNA enriched in step 2) to high-throughput sequencing; and
4) analyzing the sequencing result of step 3), if the sequencing result includes the parasite-derived DNA sequence, it is determined that the sample contains the parasite-derived DNA.

The term "cell-free DNA" refers to extracellular DNA present in body fluids, usually fragmented DNA that is different from its naturally-occurring state.

In the present disclosure, the term "genomic DNA" includes not only chromosomal DNA, but also mitochondrial DNA other than chromosomes.

In one embodiment, the sample is a mammal body fluid sample, preferably a blood, saliva, and/or urine sample, particularly a serum and/or plasma sample. The mammal is, for example, a human.

In another embodiment, selective enrichment of step 2) is performed using an amplicon-based capture and/or a hybridization-based capture. The amplicon-based capture refers to a method of amplifying a target nucleic acid fragment from a sample by using a nucleic acid amplification technology (such as a polymerase chain reaction, PCR). The hybridization-based capture refers to a method of specifically capturing/enriching a target nucleic acid fragment using a nucleic acid hybridization method.

In a specific embodiment, the amplicon-based capture is selected from the group consisting of multiplex PCR, circular PCR, circulating single-molecule amplification and resequencing technology (cSMART), bridge PCR, droplet PCR and isothermal DNA amplification, for example, multiplex PCR is used to perform the selective enrichment of step 2).

In another specific embodiment, the hybridization-based capture is selected from the group consisting of solid-phase (e.g., microarray) hybridization capture, liquid-phase hybridization capture, and inverted probe-based capture methods such as molecular inversion probes (MIP).

In another embodiment, one or more specific target sequences from the parasite genomic DNA are selectively enriched, such as 1-100, 2-50, 3-40, 4-30 or 5-20, particularly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50, preferably the specific target sequences are repeat sequences in the parasite genomic DNA.

In a specific embodiment, at least one of the specific target sequences is from the genomic DNA of one or more parasite species/variants/serotypes, for example from the genomic DNA of two or more parasite species/variants/serotypes, which is useful to determine the parasite species/variants/serotypes possibly present in the sample; in particular, at least one of the specific target sequences is a common sequence or a unique sequence in the genomic DNA of two or more parasite species/variants/serotypes; and/or at least one of the specific target sequences is a repeat sequence in the parasite genome.

In another embodiment, the parasite is selected from the group consisting of protozoan, nematode, trematode and cestode, particularly *Ancylostoma, Ascaris, Schistosoma, Echinococcus, Enterobius, Toxoplasma, Amoeba*, and more particularly *Echinococcus*, such as *Echinococcus granulosus* and/or *Echinococcus multilocularis*. Particularly, the parasite is *Schistosoma*.

In another embodiment, in step 2), one or more sets of primers or probes are used for selectively enriching the parasite-derived DNA, for example for selectively enriching one or more specific target sequences from parasitic genome(s), such as 1-100, 2-50, 3-40, 4-30, or 5-20 sets of primers or probes, particularly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 sets of primers or probes, or any value between any two of the above values. In particular, two or more primer sets can share primers.

In a specific embodiment, the length of the specific target sequence selectively enriched in step 2) is 50-500 base pairs, for example, 60-400 bp, 70-300 bp, 80-200 bp, 100-200 bp, 100-150 bp, 150-200 bp, or 50, 60, 70, 80, 90, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 160, 170, 180, 190, 200, 210, 220, 230, 240, 250, 260, 270, 280, 290, 300 bp, or any value between any two of the above values.

In another embodiment, the parasite-derived DNA selectively enriched in step 2) is derived from one or more target sequences selected from the group consisting of *Echinococcus* genomic DNA corresponding to the target sequences amplified from SEQ ID NO: 1 to 26, preferably, *Echinococcus* genomic DNA corresponding to the target sequences amplified from SEQ ID NO: 1 to 14 or SEQ ID NO: 1 to 8; and/or the selective enrichment in step 2) uses one or more sets of primers which are selected from the group consisting of SEQ ID NO: 1 to 26, for example, SEQ ID NO: 1 to 14 or SEQ ID NO: 1 to 8.

In another embodiment, wherein in step 2), the method comprises a step of using labeled primer or probe combinations to selectively enrich DNA from multiple samples respectively, combining the labeled DNA obtained from multiple samples through the selective enrichment, and performing the high-throughput sequencing of step 3) to detect multiple samples in a single run of high-throughput sequencing; wherein the number of multiple samples may be 2-10000, 3-5000, 4-3000, 5-1000, 6-500, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 150, 200, 300, 400, 500, 600, 700, 800, 900, 1000, or any value between any two of the above values; preferably, the label is selected from a fluorescent label, a short sequence tag for coding, and more preferably a short sequence tag for coding. These short sequence tags for coding are used to uniquely identify different samples and/or different libraries. Specifically, by identifying these short sequence tags for coding in the sequencing results, the source of the sample and/or the source of the library for a particular read sequence can be identified. In a specific embodiment, the short sequence tag for coding can be added during the selective enrichment step, or can also be added during the library construction process before high-throughput sequencing.

In another embodiment, an internal control fragment (ICF) that is selectively enriched with the parasite-derived DNA is used in the selective enrichment in step 2) to indicate whether the selective amplification process is successful.

In another embodiment, in the selective enrichment of step 2), an independent DNA that does not participate in the enrichment amplification and does not affect the enrichment amplification is used as a reference to normalize different samples for comparison; the independent DNA is, for example, 2-phage genomic DNA, and human genomic DNA in the sample can also be considered as a reference for normalizing.

In another embodiment, the high-throughput sequencing of step 3) is performed by using a method selected from the group consisting of: Roche/454FLX, illumina/Xten/HiSeq/MiSeq/NextSeq, Applied Biosystems/SOLID, ThermoFisher Scientific/Ion Torrent Proton, and BGI/BGISEQ-500.

In another embodiment, in the analysis of step 4), firstly, by sequence alignment, sequence fragments matching the host genomic sequence are filtered out and/or those matching the independent DNAs (such as 2-phage genomic DNA) that are additionally added as reference are filtered out from the sequencing result, so as to reduce background interference. In addition, short recognition coding sequences (such as barcode sequences) in each read can also be removed from the high-throughput sequencing results in advance.

In another embodiment, in step 4), if the number of reads of the parasite-derived DNA sequence accounts for at least 1%, 2%, 3%, 4%, 5%, 6%, 7%, 8%, 9%, 10%, 15%, 20%, 25%, 30%, 35%, or 40% of the total number of sequence reads of the sequencing result, it is determined that the sample contains the parasite-derived DNA.

In a second aspect, the present disclosure provides a method for diagnosing whether a host is suffering from a parasitic infection, comprising:
1) providing a sample from the host;
2) detecting the presence of parasite-derived DNA in the sample using the method according to any one of claims 1-16;
3) according to the result of step 2), if the parasite-derived DNA is present in the sample, it is determined that the host is suffering from parasite infection.

In addition, the present disclosure also provides a method for treating a parasitic infection in a host, comprising: performing the method of the second aspect of the present disclosure to diagnose whether the host subject is suffering from a parasitic infection; if the host subject is suffering from a parasitic infection, treating the same for the parasitic infection.

In a third aspect, the present invention provides a method for determining the efficacy of a parasitic infection treatment in a host, comprising
1) providing a sample from the host received parasite infection treatment;
2) detecting the presence of parasite-derived DNA in the sample using the method according to the first aspect;
3) according to the result of step 2), if there is no parasite-derived DNA or less amount of parasite-derived DNA in the sample compared to the amount before the treatment, the parasitic infection in the host is indicated to have been treated.

In a fourth aspect, the present disclosure provides a method for screening treatment method for a parasitic infection, comprising:
1) treating a host in need thereof with a candidate treatment for parasitic infection;
2) detecting the presence of parasite-derived DNA in the sample from the host using the method according to the first aspect;
3) according to the result of step 2), if there is no parasite-derived DNA or less amount of parasite-derived DNA in the sample compared to the amount before the treatment, the candidate treatment for parasitic infection is indicated effective.

In an embodiment of the above first to third aspects, the sample is a body fluid sample, preferably a blood, saliva, and/or urine sample, and particularly a serum and/or plasma sample. The body fluid sample may be from a mammal, such as a human.

In a fifth aspect, the present disclosure provides a kit for detecting the presence of parasite-derived DNA in a sample, comprising: a reagent for selectively enriching parasite-derived DNA in a sample, and an instruction for use.

In one embodiment, the kit is used to perform the method described in any of the foregoing aspects of the present disclosure.

In another embodiment, reagents for selectively enriching parasite-derived DNA in a sample are one or more sets of primers and/or probes, preferably one or more sets of primers, for selectively enriching one or more specific target sequences derived from parasite, for example, 1-100 sets, 2-50 sets, 3-40 sets, 4-30 sets, or 5-20 sets of primers or probes, particularly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 sets of primers or probes; in particular, the one or more sets of primers are one, more or all selected from the group consisting of SEQ ID NO: 1 to 26, for example, SEQ ID NO: 1 to 14 or SEQ ID NO: 1 to 8.

In a specific embodiment, the length of specific target sequence is 50-500 base pairs, such as 60-400 bp, 70-300 bp, 80-200 bp, 100-200 bp, 100-150 bp, 150-200 bp, or 50, 60, 70, 80, 90, 100, 110, 120, 130, 140, 150, 160, 170, 180, 190, 200, 210, 220, 230, 240, 250, 260, 270, 280, 290, 300 bp or any value between any two of the above values.

In another embodiment, the primers or probes are labeled to enable the detection of multiple samples in a single run of high-throughput sequencing. The amount of the multiple samples may be 2-10000, 3-5000, 4-3000, 5-1000, 6-500, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 150, 200, 300, 400, 500, 600, 700, 800, 900, 1000 or any value between any two of the above values. Preferably, the label is selected from a fluorescent label, a short sequence tag for coding, and more preferably a short sequence tag for coding. In a specific embodiment, the short sequence tag for coding may be 3-10 nucleotides in length, such as 3, 4, 5, 6, 7, 8, 9, or 10 nucleotides.

In another embodiment, the specific target sequences are from the genomic DNA of one or more parasite species/variants/serotypes, for example from the genomic DNA of two or more parasite species/variants/serotypes, which is useful to determine the parasite species/variants/serotypes possibly present in the sample; in particular, at least some of the specific target sequences is a common sequence or a unique sequence in the genomic DNA of two or more parasite species/variants/serotypes.

In another embodiment, at least one of the specific target sequences is a repeat sequence in the parasite genome. Multiple copies of repeat sequences in genomic DNA increase the probability of detection, thereby increasing detection sensitivity.

In another embodiment, the parasite is *Echinococcus*, such as *Echinococcus granulosus* and/or *Echinococcus multilocularis*. *Echinococcus* is the pathogen that causes echinococcosis. Therein, *Echinococcus granulosus* causes cystic echinococcosis, and *Echinococcus multilocularis* is the pathogen that causes alveolar echinococcosis.

In another embodiment, the kit further comprises an internal control fragment (ICF) for indicating whether the selective amplification process is successfully carried out, wherein each of the internal control fragments can be amplified or captured using a pair of primers and/or probes for an specific target sequence. The internal control fragments usually have properties equivalent to specific target sequences, for example, a length of 50 to 170 bp, each fragment comprising the recognition region corresponding to a pair of primers out of a primer panel, and the amplified product having a GC content and length equivalent to those of target amplification product on the hydatid genome obtained using the same primer. The sequence of the ICF amplification product is known, and prominently different from the sequence of the target amplification product on the *Echinococcus* genome, which can be easily distinguished during subsequent data analysis.

In another embodiment, the kit further comprises at least one reagent selected from the group consisting of a DNA extraction reagent, a PCR reagent, and a high-throughput sequencing reagent.

In an embodiment of the kit, the sample to be detected is a body fluid sample, preferably a blood sample, saliva and/or urine sample, particularly a serum and/or plasma sample. The body fluid sample may be from a mammal, such as a human. In addition, the kit of the present invention may further comprise a therapeutic agent for parasitic infection, so as to use the kit to treat a parasitic infection in a host In a sixth aspect, the present invention also provides the use of a reagent for selectively enriching parasite-derived DNA in a sample in the preparation of a kit for implementing the methods in any of the foregoing aspects of the present disclosure.

EXAMPLES

1. Peripheral Blood Collection

Peripheral blood sample of the subject was collected with a needle of 7 gauge or larger than 7 gauge, and the blood sample was collected into cell free DNA blood collection tube (Streck, Cat. 218997) in a volume of 10 mL. The collected blood samples were stored at room temperature for at least 30 minutes, then transferred to 4° C. for refrigerated storage and transportation. The plasma was separated within 96 hours.

2. Plasma Separation

The blood sample was centrifuged at 1,600 g at 4° C. for 10 min. The supernatant (plasma) was collected and pipetted into multiple 1.5 mL centrifuge tubes. During the aspiration of the plasma, be careful not to touch the white blood cells in the middle layer and the red blood cells on the tube wall. During the process, handle gently to avoid contamination by splashing the plasma on the tube cap or the lip.

The above supernatant was centrifuged at 16,000 g at 4° C. for 10 min to remove residual cells as well as cell debris. The supernatant was transferred again into a new 1.5 mL centrifuge tube to obtain the plasma needed. When transferring the supernatant, avoid touching the cell residue at the bottom of the tube with the pipette tip. About 50 μL of plasma was left at the bottom of the tube.

3. Cell-Free DNA Extraction

In this example, a commercially available blood nucleic acid extraction kit (QIAGEN Circulating Nucleic Acid Extraction Kit) was used for extraction. Other methods based on silica gel column adsorption, magnetic bead capture, or DNA precipitation may also be used.

3 mL of separated plasma was used for cell-free DNA extraction with QIAGEN Circulating Nucleic Acid Extraction Kit (QIAGEN, Cat. 55114).

3.1 Plasma Protein Digestion

In a 50 mL centrifuge tube, 300 μL of proteinase K (20 mg/mL), 3 mL plasma (adjustable as need, when the initial plasma volume changes, the extraction buffer and elution volume change accordingly), 2.4 mL of buffer ACL and 5.6 μL of carrier RNA (0.2 μg/μL) were added and mixed. The mixture was placed into a constant temperature water bath and incubated at 60° C. for 60 min.

3.2 DNA Precipitation

After the completion of incubation, the centrifuge tube was taken out, 5.4 mL of Buffer ACB was added, mixed thoroughly by pulse-vortexing. The mixture was incubated on ice for 5 minutes. Meanwhile, the vacuum pump (negative pressure of −800 to −900 mbar) compatible with the kit, the vacuum base (QIAGEN, Cat. 19413), the binding column and tube extender provided in the kit were set up, leaving the collection tube matching the binding column available.

3.3 DNA Binding

The DNA-buffer mixture in the centrifuge tube was applied into the tube extender of the column, the vacuum pump was switched on, and the mixture was drawn through the tube extender, binding column and vacuum connector in turn, and cell-free DNA was bound to the binding column.

3.4 Washing

After the mixture has been drawn through, the tube extender was removed and the vacuum pump was switched off. 600 μL of ACW1 was applied to the binding column, and the vacuum pump was switched on. This was the first washing.

After ACW1 has been completely drawn through, the vacuum pump was switched off. 750 μL of ACW2 was applied to the binding column, and the vacuum pump was switched on. This was the second washing.

After ACW2 has been completely drawn through, the vacuum pump was switched off. 750 μL of absolute ethanol was applied to the binding column, and the vacuum pump was switched on. This was the third washing.

3.5 Removing Solvent by Centrifuge

After the absolute ethanol has been drawn through, the vacuum pump was switched off. The binding column was removed and place in the collection tube matching the binding column. The tube was centrifuged at 16,000 g at room temperature for 3 minutes to completely remove the remaining absolute ethanol in the column.

3.6 Drying

After the completion of centrifugation, the binding column was placed into a new 1.5 mL centrifuge tube and incubated at 56° C. for 10 min.

3.7 Dissolving DNA

After the completion of drying, 50 μL of AVE (adjustable as need) was applied to the center of the membrane of the binding column, incubated for 3 minutes for complete elution of bound DNA. The 1.5 mL tube was centrifuged at 16,000 g at room temperature for 1 minute to elute and collect the DNA.

3.8 Quality Control

The extracted cell-free DNA was precisely quantified using the commercial kit Qubit® dsDNA HS Assay Kit (Qubit, Q32854). Samples with a cell-free DNA concentration below 0.2 ng/μL were excluded and fed back to the receiver to arrange for re-blood draw. After the cell-free DNA extraction step has been completed, the extracted cell-free DNA was frozen at −80° C. until use.

4. Amplification and Enrichment of Echinococcus-Specific Fragments

The enrichment method used in this example was to amplify multiple sites of repeat sequences on Echinococcus genome with multiple pairs of primers. The self-developed Echinococcus-specific amplification primers were used to amplify and enrich the cell-free DNA of the subjects.

A trace mount of ICF fragment was added to the amplification system. The ICF fragment, along with the Echinococcus genomic DNA in the cell-free DNA, served as templates to participate in the amplification process and as a monitoring system for the success of a single sample amplification.

A certain amount of exogenous 2-phage DNA was added as an internal reference in the amplification system, which was in the amplification system but did not participate in the amplification process, and was used for normalizing the positive sequences in the sequencing results.

PCR Amplification System

| | |
|---|---|
| Premix Ex Taq DNA Polymerase HS Version | 10 μL |
| Enrichment primer set (40 μM) | 1 μL |
| ICF mix (10 ag/μL each) | 0.5 μL |
| λ-DNA (10 ng/uL) | 0.5 μL |
| Cell-free DNA template | 8 μL |
| Total volume | 20 μL |

Note:
Premix Ex Taq DNA Polymerase HS Version (Cat. RR030A) is a commercial premixed PCR reaction solution from TAKARA, which contains TaKaRa Ex Taq HS (1.25 U/25 μL), PCR Buffer (containing 4 mM Mg$^{2+}$), dNTP (0.4 mM each), anti-Taq antibody.

The sequences of the enrichment primers are shown in SEQ ID NO: 1 to 26. As an example, 1F and 1R (SEQ ID NO: 1 and 2) constitute a pair of primers, which can specifically amplify the corresponding repeat on the Echinococcus genome when using the Echinococcus genome as a template. Accordingly, 2F/2R, 3F/3R, etc. are primer pairs respectively.

| SEQ ID NO: | Primer No. | Sequence | Minimal product length |
|---|---|---|---|
| 1 | 1F | 5'-CACTGTGACGTCATCTGGCCT-3' | ~70 |
| 2 | 1R | 5'-TCAGGTGACGTAATGGAGGGTCT-3' | |
| 3 | 2F | 5'-TCTGCTGCTTGCATTCACAC-3' | ~84 |
| 4 | 2R | 5'-CAAATGCTCGGTACACCACG-3' | |
| 5 | 3F | 5'-GTCGGTCGCATTAGTAGCTC-3' | ~74 |
| 6 | 3R | 5'-AACAAACCGAACACACCAAAC-3' | |
| 7 | 4F | 5'-CTGCAATAGCACCCAATTCACA-3' | ~86 |
| 8 | 4R | 5'-GAAGGAGTATCGTTGGTACGCT-3' | |
| 9 | 5F | 5'-TTCGTGCTACGACTTTCTCCAC-3' | ~72 |
| 10 | 5R | 5'-GGAGTGCAAATGAAGTAGATGCG-3' | |
| 11 | 6F | 5'-CCACCCAGCGAGGTACAAG-3' | ~75 |
| 12 | 6R | 5'-AGTGGTTTATCCCTCGGTTCTG-3' | |
| 13 | 7F | 5'-TGGCGCAACACCTTGTAGAT-3' | ~87 |
| 14 | 7R | 5'-GAAGGTGAAGGTGCCGAAGA-3' | |
| 15 | 8F | 5'-AGTAGCGGAACGGTGGATTT-3' | ~83 |
| 16 | 8R | 5'-ACAATGGCCGGTAGTGAAGA-3' | |
| 17 | 9F | 5'-GTTTCACACCGACAACTGCAA-3' | ~76 |
| 18 | 9R | 5'-TGAGTCGAAGGCGAACACC-3' | |
| 19 | 10F | 5'-GGATCCGTCGATGTTAGCGT-3' | ~71 |
| 20 | 10R | 5'-CCGCCATAGAGGGTAGATGC-3' | |
| 21 | 11F | 5'-CGGGACACATCCTAACTGGT-3' | ~83 |
| 22 | 11R | 5'-CCGGTCATCCATGGGGATTG-3' | |
| 23 | 12F | 5'-CAGAGGCTCGTTTGTGGTCA-3' | ~73 |
| 24 | 12R | 5'-GGTGCACATTAAATACCAAAACCC-3' | |
| 25 | 13F | 5'-AGCACTCCTCATCAGTCAACTC-3' | ~82 |
| 26 | 13R | 5'-CTGAAACATGCTAAAGGTATGCGT-3' | |

A synthetic internal control fragment (ICF) was added to the amplification system as a monitoring system for the success of sample amplification. The sequence information of ICF is shown in the table below. ICF-1 to ICF-6 correspond to the amplified products of primers 1F/1R, 3F/3R, 4F/4R, 5F/5R, 6F/6R, and 7F/7R, respectively.

| SEQ ID NO: | No. | Amplicon sequence |
|---|---|---|
| 27 | ICF-1 | 5'-CACTG TGACG TCATC TGGCC TGCAG CAAAG GTATC ATCGG CATAT TCTAA GTCAG TTCAA CTACC TAGAC CCTCC ATTAC GTCAC CTGA-3' |
| 28 | ICF-2 | 5'-TCTGC TGCTT GCATT CACAC GCAGC TCAAA AGTGT CCCAG GTCTA CTGAA ACCCC CGAAG ACCTC GTGGT GTACC GAGCA TTTG-3' |
| 29 | ICF-3 | 5'-CTGCA ATAGC ACCCAATTCA CAGCA TCAAG TTCCA AGCAC AGTCA TTCGC TCTAC TCGAC TAGCG TACCA ACGAT ACTCC TTC-3' |

-continued

| SEQ ID NO: | No. | Amplicon sequence |
|---|---|---|
| 30 | ICF-4 | 5'-TTCGT GCTAC GACTT TCTCC ACCGT CATGG CAGTC ACGCT CTAAT CCATC GCTTC GCATC TACTT CATTT GCACT CC-3' |
| 31 | ICF-5 | 5'-CCACC CAGCG AGGTA CAAGC CAATG ATTCG GTTAG TCTGC TGATG GCTCG CTTCA GAACC GAGGG ATAAA CCACT-3' |
| 32 | ICF-6 | 5'-TGGCG CAACA CCTTG TAGAT CCCGT CATCG TCAAT GATCA GTTGA GGTGG TTGGG ACATC GCTTT CTTCG GCACC TTCAC CTTC-3' |

PCR Amplification Conditions

| | | |
|---|---|---|
| 95° C. | 5 min | |
| 95° C. | 30 s | 10 cycles |
| 68~58° C., −1° C./cycling (touch down) | 30 s | |
| 72° C. | 15 s | |
| 95° C. | 30 s | 30 cycles |
| 58° C. | 30 s | |
| 72° C. | 15 s | |
| 72° C. | 5 min | |
| 4° C. | hold | |

After the completion of PCR amplification, the products were purified with commercial AMPure XP Beads (Beckman Coulter, A63881) and a home-made polyethylene glycol buffer (PEG buffer).

Formulation of PEG Buffer

| | |
|---|---|
| PEG8000 (Sigma, 89510) | 40 g |
| 1M EDTA (pH 8.0) | 1 mL |
| ddH$_2$O | Make up to 100 mL |

50 μL of AMPure XP Beads, 20 μL of PCR amplification product, and 5 μL of PEG buffer were added to a 1.5 mL centrifuge tube, mixed thoroughly, and stood at room temperature for 5 min.

The centrifuge tube was placed on a magnetic stand for 5 minutes. After the magnetic beads were fully attached to the side wall, the supernatant was discarded.

200 μL of freshly prepared 80% ethanol was added to the centrifuge tube. The centrifuge tube was kept on a magnetic stand, turned upside down in front-back and left-right direction, two times each, stood vertically for 30 seconds, and then the ethanol was discarded.

The previous wash step was repeated once.

The ethanol in the centrifuge tube was removed completely, the centrifuge tube was maintained on the magnetic stand, and the tube was open and dried.

After about 5 min, when the centrifuge tube was fully dried, the centrifuge tube was removed from the magnetic stand. 22 μL of 0.1×TE was added, mixed gently, and stood at room temperature for 5 min.

The centrifuge tube was placed on a magnetic stand for 5 minutes. After the magnetic beads were fully attached to the side wall, 20 μL of the supernatant was collected into a new PCR tube for later use.

5. High-Throughput Sequencing 5.1 Library Construction

Qubit® dsDNA HS Assay Kit was used to accurately quantify purified PCR products. 10 ng of PCR products was taken and NEBNext® Ultra™ II DNA Library Prep Kit for Illumina® (NEB, E7645S) was used to construct the library. Unless otherwise specified, the procedures below, as well as reagents, oligonucleotides such as primers and adaptors, are listed in the manufacturer's manual, including but not limited to NEBNext® Ultra™ II DNA Library Prep Kit for Illumina® and NEBNext® Multiplex Oligos for Illumina®.

5.1.1 End Preparation

The PCR product was diluted to 25 μL with 0.1×TE buffer, and the following components were sequentially added to the PCR tube:

| | |
|---|---|
| NEBNext Ultra II End Prep Reaction Buffer | 3.5 μL |
| NEBNext Ultra II End Prep Enzym Mix | 1.5 μL |
| Purified PCR product | 25 μL |
| Total volume | 30 μL |

The mixture was pipetted up and down by a 100 μL pipette and subjected to quick spin to collect all liquid from the sides of the tube.

The tube was placed in a PCR machine, and the program was set as:

| Temperature | Reaction time |
|---|---|
| 20° C. | 30 min |
| 65° C. | 30 min |
| 4° C. | Hold |

5.1.2 Adaptor Ligation

The following components were added to a tube:

| | |
|---|---|
| End Prep Reaction Mixture (Step 5.1.1) | 30 μL |
| NEBNext Ultra II Ligation Master Mix | 15 μL |
| NEBNext Ligation Enhancer | 0.5 μL |
| NEBNext Adaptor for Illumina | 1.5 μL |
| Total volume | 47 μL |

The mixture was pipetted up and down by a 100 μL pipette and subjected to quick spin to collect all liquid from the sides of the tube.

The tube was placed in a PCR machine, and the program was set as:

| Temperature | Reaction time |
|---|---|
| 20° C. | 15 min |

After the completion of reaction, the PCR tube was taken out, 2 μL of USER Enzyme was added, mixed by pipetting, and subjected to quick spin to collect all liquid from the sides of the tube.

The tube was placed in a PCR machine, and the program was set as:

| Temperature | Reaction time |
|---|---|
| 37° C. | 15 min |

5.1.3 Purification of Adaptor-Ligated DNA

In another 1.5 mL centrifuge tube, the ligation product and 25 μL of AMPure XP Beads were added, mixed thoroughly and incubated at room temperature for 5 min.

The centrifuge tube was placed on a magnetic stand for 5 minutes. After the magnetic beads were completely attached to the sides, the supernatant was transferred to a new 1.5 mL centrifuge tube.

25 μL of AMPure XP Beads was added to the centrifuge tube, mixed thoroughly and incubated at room temperature for 5 min.

The centrifuge tube was placed on a magnetic stand for 5 minutes. After the magnetic beads were completely attached to the sides, the supernatant was discarded.

200 μL of 80% freshly prepared ethanol was added to the centrifuge tube while in the magnetic stand. The tube was inverted in front-back and left-right directions, twice each direction, and then incubated vertically for 30 seconds. After the incubation, the ethanol was discarded.

The previous wash step was repeated once.

The ethanol was removed completely from the centrifuge tube, the centrifuge tube was maintained on the magnetic stand, and the lid was open for drying.

After about 5 min, when the centrifuge tube was completely dried, the tube was removed from the magnetic stand, 17 μL of 0.1×TE buffer was added, mixed gently, and incubated at room temperature for 5 min.

The centrifuge tube was placed on a magnetic stand for 5 minutes. After the magnetic beads were fully attached to the sides, 15 μL of the supernatant was transferred to a new PCR tube for later use.

5.1.4 PCR Amplification

The following components were added to the above PCR tube:

| | |
|---|---|
| Adaptor-ligated DNA fragments (Step 5.1.3) | 15 μL |
| NEBNext Ultra II Q5 Master Mix | 25 μL |
| Index Primer | 5 μL |
| Universal PCR Primer | 5 μL |
| Total volume | 50 μL |

The tube was placed in a PCR machine and the program was set as:

| Temperature | Reaction time | |
|---|---|---|
| 98° C. | 30 s | |
| 98° C. | 10 s | 6 cycles |
| 65° C. | 75 s | |
| 65° C. | 5 min | |
| 4° C. | hold | |

5.1.5 Purification of PCR Products

In a 1.5 mL centrifuge tube, the PCR amplification product and 45 μL of AMPure XP Beads were added, mixed thoroughly, and incubated at room temperature for 5 min. The centrifuge tube was placed on a magnetic stand and the PCR product was purified according to the method in Step 5.1.3. After purification, the product was eluted by 33 μL of 0.1×TE, and 30 μL of the eluate was transferred into a new 1.5 mL centrifuge tube for later use.

5.2 High-Throughput Sequencing

According to the manufacturer's instructions, the constructed library was subjected to high-throughput sequencing. The sequencing platform was Illumina MiSeq 500. 2M of reads were generated for each sample. Different amounts of reads may be generated as required.

6. Data Analysis and Result Determination

Data analysis can be performed manually or assisted by various bioinformatics analysis software. In the data analysis of this example, commercially available analysis software and self-developed analysis software were used. Although not required, the analysis software could significantly increase analysis efficiency. High-throughput sequencing raw data was downloaded in fastq format. The sequencing data was input into self-developed bioinformatics analysis software.

Each short sequence generated in high-throughput sequencing is often referred to a read. The short fragment sequence information of multiple samples generated by high-throughput sequencing in the previous step was input into the analysis software; first, these sequences were aligned to the genomic sequence of the λ-phage, and the amount of reads that were successfully matched was calculated as the denominator of the normalization ratio (λ-DNA is in the amplification system but does not participate in the amplification process, which can be used as a reference); then the unaligned sequence was further aligned to the human reference genome sequence, and the successfully aligned sequences were abandoned, while the remaining sequences were used for subsequent analysis; these sequences were aligned to the repeat regions of two species of the *Echinococcus* (*Echinococcus granulosus* and *Echinococcus multilocularis*) genome. The read successfully matching the short sequences of the repeat sequence regions of the *Echinococcus* genome was considered to be the sequence from the parasite. The positive rate and the normalization ratio of the two *Echinococcus* reference genomes were calculated (for the positive rate, the denominator is the number of total reads of the sample, that is, the data of the short sequence Set R3; For this normalization ratio, the denominator is the number of reads that match the 2-phage genome i.e., the short fragment sequence data set RC).

In addition, when no additional 2-DNA was added to the amplification system, the number of reads successfully mapped to the human genome can also be used as a basis for subsequent normalization processing, replacing the additionally added 2-DNA.

Data Analysis Software Processing

Pre-step (pre-processing): the short sequences were classified according to the barcode information of the unique sample, and the barcode was removed from the short sequence. The pre-processed short-sequence data set was marked as R1.

Step 1 (alignment to 2-phage reference genome): bowtie2 alignment tool (http://bowtie-bio.sourceforge.net/bowtie2/index.shtml, B. Langmead & SL Salzberg, Fast gapped-read alignment with Bowtie 2, Nature Methods, 9: 357-359 (2012)) was used to align the short sequence data set R1 to the 2-phage reference genome. The number of successfully matched reads was recorded as the short fragment sequence data set RC. According to the alignment result, these short fragments sequences successfully aligned to the 2-phage reference genome were discarded, and short fragment sequences that were not successfully aligned to the 2-phage reference genome were collected, and these short fragment sequences were marked as short fragment sequence data set R2.

Step 2 (alignment to human reference genome): bowtie2 alignment tool was used to align the short fragment sequence data set R2 to the human reference genome. According to the results of the alignment, these short fragment sequences that were successfully aligned to the human reference genome were discarded, short fragment sequences that were not successfully aligned to the human reference genome were collected, and these short sequences were marked as short fragment sequence data set R3.

Step 3 (alignment to the repeat regions of the *Echinococcus* genome): bowtie2 alignment tool was used to align the short fragment sequence data set R3 to the repeat regions of the two *Echinococcus* genomes, and the successfully aligned data set was recorded as R4. According to the results of the alignment, the positive rates of successfully aligned to the repeat regions of the *Echinococcus* genome were calculated for each sample, and the normalization ratio was also calculated, wherein for the selected sample A, the positive rate was calculated as the percentage of the sequence number of the sample A in the short sequence data set R4 to the number of the short sequence in R3. The normalization ratio was calculated as the number of sequences of sample A in the short sequence data set R4 divided by the number of sequences of the short sequence data set RC.

7. Analysis of Mock Echinococcosis Samples

According to the schemes of examples 2 and 3, the cell-free DNA from the hydatid cyst fluid (HCF) of the patients diagnosed with echinococcosis was extracted and added to the amplification system of Example 4 as a Mock *Echinococcus* sample. A sample without hydatid cyst fluid containing cell-free DNA was used as a control sample. According to the schemes of examples 4 to 6, high-throughput sequencing was performed after the selective enrichment and the sequencing results were analyzed. In the selective enrichment, 2 fg cell-free DNA from cystic fluid sample was used as a template for the Mock *Echinococcus* sample. The Mock *Echinococcus* sample was tested 3 times and the control sample was tested once. The analysis results of the 4 samples were shown in the following table. In the sequencing results, the proportion of reads of *Echinococcus* in the total reads was called the positive rate herein. From this, it can be seen that the method of the present disclosure can significantly distinguish a positive Mock sample from a control sample without hydatid DNA.

| DNA sample No. | Positive rate | *Echinococcus* reads/total reads |
| --- | --- | --- |
| Mock *Echinococcus* sample 1 (2 fg) | 95.46% | 384432/402720 |
| Mock *Echinococcus* sample 2 (2 fg) | 95.76% | 416071/434492 |
| Mock *Echinococcus* sample 3 (2 fg) | 95.72% | 510087/532877 |
| Control sample (0 fg) | 0.06% | 151/243889 |

8. Correlation Between Positive Rate and Template Amount

Referring to the operation of Example 7, the amount of cell-free DNA from cystic fluid sample as a template for selective enrichment was adjusted (see the table below for specific amount), and the Mock *Echinococcus* DNA sample was used for multiple analysis. The table below shows the results of the analysis by adding different amounts of cell-free DNA from hydatid cyst fluid as a template. It can be noticed that the ratio of positive reads varies in samples containing the same amount of DNA. The reason may be that since the concentration of the DNA sample used as the template was very low (1 fg/ul), the exact amount of the sample cannot be guaranteed when pipetting the DNA samples with very small amounts (1 fg/2 fg/4 fg), resulting in different samples having different proportions of positive reads. However, it can be found that the overall trend is still clear: the method of the present invention can be used to a cell-free DNA sample having an amount as small as 1 fg. As the amount of cell-free DNA in the sample increased, the positive rate in the analysis results also increased.

As empirical knowledge, regarding the correspondence between the amount of DNA and the *Echinococcus* genome, the following conversion relationship may be used: 100 fg DNA is approximately equivalent to the genomic DNA from one *Echinococcus* cell.

| *Echinococcus* template DNA | Positive rate | Positive reads amount/ total reads amount |
| --- | --- | --- |
| 1 pg | 98.32% | 1309866/1332207 |
| 100 fg | 97.76% | 1844782/1887096 |
| 100 fg | 93.42% | 1572122/1682807 |
| 10 fg | 84.75% | 751238/886399 |
| 10 fg | 76.75% | 845829/1102020 |
| 10 fg | 99.07% | 295908/298675 |
| 10 fg | 97.28% | 1539316/1582334 |
| 4 fg | 90.91% | 36091/39700 |
| 4 fg | 79.33% | 894357/1127401 |
| 4 fg | 76.11% | 985634/1295027 |
| 2 fg | 90.36% | 132195/146292 |
| 2 fg | 95.30% | 344580/361572 |
| 2 fg | 34.32% | 596946/1739247 |
| 2 fg | 89.77% | 110588/123192 |
| 2 fg | 88.29% | 1152676/1305612 |
| 1 fg | 28.44% | 82801/291126 |
| 1 fg | 53.86% | 47349/87915 |
| 1 fg | 0.13% | 1972/1528485 |
| 1 fg | 3.60% | 3958/110029 |
| 0 fg | 0.07% | 173/241072 |
| 0 fg | 0.40% | 5854/1448181 |
| 0 fg | 1.43% | 7505/523264 |
| 0 fg | 0.13% | 16/12494 |

-continued

| Echinococcus template DNA | Positive rate | Positive reads amount/ total reads amount |
|---|---|---|
| 0 fg | 0.01% | 39/685320 |
| 0 fg | 2.33% | 10274/440722 |
| 0 fg | 0.08% | 55/68072 |

9. Analysis with Large Sample Size

A plurality of patients diagnosed with echinococcosis and healthy controls were selected. According to the schemes of examples 1 to 6, the cell-free DNA of the subjects was collected, subjected to high-throughput sequencing after selective enrichment, and the sequencing results were analyzed. Therein, a cell-free DNA sample from 1 mL of blood sample was used as the template for selective enrichment. Specifically, 15 patients with echinococcosis (P1 to P15), 5 Chinese minority healthy controls (C1 to C5), and 19 Han Chinese healthy controls (C6 to C24) were included. The analysis results are shown in the following table. The positive rate of *Echinococcus* DNA detected in healthy control samples was very low, with the highest no more than 3% (C13). However, patients with echinococcosis had significantly higher positive rates of *Echinococcus* DNA, except for patients P4, P5, P10, P11, and P12. Further imaging and tissue biopsy tests revealed that patient P4 had normal cysts instead of echinococcosis; patient P11 had calcificated lesions but no fertile cysts. It can be inferred that patient P4 was misdiagnosed; patient P11 had echinococcosis, but no longer had live *Echinococcus* infection at the time of sampling. Patients P5, P10, and P12 lost contact and could not be confirmed.

From this, it can be seen that the method of the present disclosure can not only distinguish significantly between patients with echinococcosis and healthy control subjects, but also distinguish between the current infection status and the previous infection status.

|  | Sample No. | Positive rate | Positive read number/ Total read number |
|---|---|---|---|
| Plasma sample of patients with echinococcosis | P1 | 82.74% | 716347/865783 |
|  | P2 | 15.74% | 730996/4643015 |
|  | P3 | 96.94% | 2771184/2858568 |
|  | P4 | 0.56% | 6103/1087397 |
|  | P5 | 0.22% | 1939/873576 |
|  | P6 | 89.45% | 576327/644303 |

-continued

|  | Sample No. | Positive rate | Positive read number/ Total read number |
|---|---|---|---|
|  | P7 | 41.03% | 59394/144761 |
|  | P8 | 92.56% | 9549199/10316521 |
|  | P9 | 86.66% | 2806646/3238676 |
|  | P10 | 0.76% | 2261/297277 |
|  | P11 | 0.01% | 105/1715568 |
|  | P12 | 0.01% | 9/148553 |
|  | P13 | 98.67% | 3980503/4033964 |
|  | P14 | 95.62% | 3866515/4043646 |
|  | P15 | 94.13% | 4093473/4348768 |
| Plasma sample of Chinese minority healthy controls | C1 | 0.00% | 0/56982 |
|  | C2 | 0.01% | 13/88010 |
|  | C3 | 0.02% | 13/82132 |
|  | C4 | 0.01% | 10/97094 |
|  | C5 | 0.01% | 4/36335 |
| Plasma sample of Han Chinese healthy controls | C6 | 0.32% | 10482/3242969 |
|  | C7 | 0.55% | 638/115635 |
|  | C8 | 0.00% | 5/145074 |
|  | C9 | 0.01% | 71/1162033 |
|  | C10 | 0.11% | 1458/1359908 |
|  | C11 | 0.01% | 26/470973 |
|  | C12 | 0.00% | 218/4559075 |
|  | C13 | 0.01% | 18/345153 |
|  | C14 | 0.01% | 9/162544 |
|  | C15 | 0.29% | 291/99795 |
|  | C16 | 0.38% | 2831/735973 |
|  | C17 | 0.06% | 233/370370 |
|  | C18 | 3.08% | 10414/338321 |
|  | C19 | 0.21% | 2193/1064023 |
|  | C20 | 0.45% | 730/162373 |
|  | C21 | 0.01% | 34/566948 |
|  | C22 | 0.01% | 18/167408 |
|  | C23 | 0.01% | 11/100887 |
|  | C24 | 0.01% | 4/31851 |

10. Calculation of Normalization Ratio for Mock *Echinococcus* Samples

Referring to Example 7, different amounts of cell-free DNA from hydatid cyst fluid were added to the amplification system of Example 4 as Mock *Echinococcus* samples, and correspondingly, samples without cell-free DNA from hydatid cyst fluid were used as control. According to the schemes of examples 4 to 6, high-throughput sequencing was performed after selective enrichment and the sequencing results were analyzed. In the sequencing results, the proportion of *Echinococcus* sequence reads in the total reads is called herein the positive rate. The ratio of *Echinococcus* sequence reads to λ-phage DNA sequence reads is referred to herein as the normalization ratio.

| Amount of λ DNA | Amount of hydatid template DNA | Proportion of reads aligned to λ DNA | Amount of reads aligned to λ DNA | Proportion of reads aligned to repeats | Amount of reads aligned to repeats | Normalization ratio |
|---|---|---|---|---|---|---|
| 5 ng | 10 fg | 0.46% | 2851 | 95.79% | 530949 | 186.23255 |
|  | 5 fg | 1.09% | 6952 | 92.76% | 527088 | 75.81818 |
|  | 2 fg | 3.23% | 22566 | 66.97% | 436411 | 19.33932 |
|  | 0 fg | 19.80% | 127571 | 0.00% | 17 | 0.00013 |

11. Analysis of Mock Infection Plasma Samples

Using the cell-free DNA from hydatid cyst fluid described in Example 7, different amounts of cell-free DNA (0fg, 5 fg, 10 fg) from hydatid cyst fluid were added to the plasma of normal controls as the Mock infected subject plasma samples and accordingly, a sample without cell-free DNA from hydatid cyst fluid was used as a control sample (NTC). According to the scheme of Example 3, cell-free DNA in the Mock infected subject plasma samples was extracted, subjected to high-throughput sequencing after selective enrichment, and the sequencing results were analyzed. In the sequencing results shown in the table, the proportion of *Echinococcus* sequence reads in the total reads is called the positive rate herein. It can be seen that, using the method of the present disclosure, it is possible to detect a Mock infected subject plasma sample with a concentration as low as 5 fg/mL.

| Amount of λ DNA | Amount of hydatid template DNA per mL of plasma | Proportion of reads aligned to λ DNA | Amount of reads aligned to λ DNA | Proportion of reads aligned to repeats | Amount of reads aligned to repeats | Normalization ratio |
|---|---|---|---|---|---|---|
| 5 ng | NTC | 31.89% | 171285 | 0.00% | 9 | 0.00005 |
|  | 0 fg | 18.38% | 6690 | 0.00% | 1 | 0.00015 |
|  | 5 fg | 0.35% | 1283 | 96.14% | 348118 | 271.33125 |
|  | 10 fg | 2.02% | 9219 | 97.31% | 432856 | 46.95260 |

NTC: no template control. The cell-free DNA in this sample is replaced with water. The remaining 0 fg, 5 fg, and 10 fg samples are mock infection samples obtained by adding corresponding amounts of *Echinococcus* DNA to normal human plasma, and the background is the cell-free DNA in 1 mL of normal human plasma.

---

What is claimed is:

1. A method of detecting parasite-derived DNA in a sample, comprising
1) Extracting DNA from the sample;
2) Selectively enriching the parasite-derived DNA in the DNA obtained in step 1) by amplifying the DNA with at least one primer pair selected from the group consisting of SEQ ID NO: 1 and 2, SEQ ID NO: 3 and 4, SEQ ID NO: 5 and 6, SEQ ID NO: 7 and 8, SEQ ID NO: 9 and 10, SEQ ID NO: 11 and 12, SEQ ID NO: 13 and 14, SEQ ID NO: 15 and 16, SEQ ID NO: 17 and 18, SEQ ID NO: 19 and 20, SEQ ID NO: 21 and 22, SEQ ID NO: 23 and 24, and SEQ ID NO: 25 and 26;
3) Subjecting the DNA enriched in step 2) to high-throughput sequencing; and
4) Analyzing the sequencing result of step 3), wherein the presence of the parasite-derived DNA sequence indicates that the sample contains the parasite-derived DNA, and the parasite is *Echinococcus*.

2. The method according to claim 1, wherein step 2) further comprises enriching and amplifying an internal control fragment (ICF) along with the parasite-derived DNA for indicating whether the selective enrichment and amplification succeeds or not.

3. The method according to claim 1, wherein the selective enrichment of step 2) is performed by using an amplicon-based capture and/or a hybridization-based capture.

4. The method according to claim 3, wherein the amplicon-based capture is selected from the group consisting of multiplex PCR, circular PCR, circulating single-molecule amplification and resequencing technology, bridge PCR, droplet PCR and isothermal DNA amplification.

5. The method according to claim 3, wherein the hybridization-based capture is selected from the group consisting of solid-phase hybridization capture, liquid-phase hybridization capture and molecular inversion probe capture.

6. The method according to claim 3, wherein one or more specific target sequences from the parasite genomic DNA is selectively enriched.

7. The method according to claim 6, wherein at least one of the specific target sequences is from the genomic DNA of one or more parasite species/variants/serotypes, which is useful to determine the parasite species/variants/serotypes possibly present in the sample.

8. The method according to claim 1, wherein the length of the specific target sequences selectively enriched in step 2) is 50-500 bp.

9. The method according to claim 1, wherein in step 2), primers are labeled with a label and used to selectively enrich DNA from multiple samples respectively, DNA with labeled primers obtained by the selective enrichment from multiple samples is combined, and the high-throughput sequencing of step 3) is performed to detect multiple samples in a single run of high-throughput sequencing; and wherein the label is selected from the group consisting of a fluorescent label and a short sequence tag for coding.

10. The method according to claim 1, wherein in the analysis of step 4), fragment sequences matching the host genomic sequence are first filtered out from the sequencing results by sequence alignment to reduce background interference.

11. The method according to claim 1, wherein in step 4), the sequencing result is represented as a read of a sequence and the sample is determined to contain the parasite-derived DNA if the number of reads of the parasite-derived DNA sequence accounts for at least 1% of the total number of sequence reads of the sequencing result.

12. The method according to claim 1, wherein in the selective enrichment of step 2), an independent DNA that does not participate in the enrichment amplification and does not affect the enrichment amplification is used as a reference to normalize different samples for comparison.

13. The method according to claim 1, wherein the parasite is *Echinococcus* selected from the group consisting of *Echinococcus granulosus* and *Echinococcus multilocularis*.

14. The method according to claim 1, wherein the selective enrichment in step 2) uses one or more primer pairs selected from the group consisting of SEQ ID NO: 1 and 2, SEQ ID NO: 3 and 4, SEQ ID NO: 5 and 6, and SEQ ID NO: 7 and 8, SEQ ID NO: 9 and 10, SEQ ID NO: 11 and 12, and SEQ ID NO: 13 and 14.

15. The method according to claim 1, wherein the selective enrichment in step 2) uses one or more primer pairs selected from the group consisting of SEQ ID NO: 1 and 2, SEQ ID NO: 3 and 4, SEQ ID NO: 5 and 6, and SEQ ID NO: 7 and 8.

16. The method according to claim 1, wherein the primer pair consists of SEQ ID NO: 1 and SEQ ID NO: 2.

17. The method according to claim 9, wherein the number of samples is 2 to 10,000.

* * * * *